US006344186B1

(12) United States Patent
Hansenne et al.

(10) Patent No.: US 6,344,186 B1
(45) Date of Patent: *Feb. 5, 2002

(54) OIL-IN-WATER EMULSIONS CONTAINING A 1,3,5-TRIAZINE DERIVATIVE AND A COPOLYOL SILICONE AND COSMETIC APPLICATIONS

(75) Inventors: Isabelle Hansenne; Martin Josso, both of Paris; Laurent Nodari, Argenteuil, all of (FR)

(73) Assignee: Societe L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,739

(22) PCT Filed: Jan. 18, 2000

(86) PCT No.: PCT/FR98/02425

§ 371 Date: Dec. 22, 1999

§ 102(e) Date: Dec. 22, 1999

(87) PCT Pub. No.: WO99/29291

PCT Pub. Date: Jun. 17, 1999

(30) Foreign Application Priority Data

Dec. 4, 1997 (FR) ............................................. 97 15310

(51) Int. Cl.$^7$ ................................................. A61K 7/44
(52) U.S. Cl. .................... 424/60; 424/70.1; 424/70.11; 424/70.12; 424/70.31; 514/938; 514/941
(58) Field of Search ............................. 424/70.1, 70.11, 424/70.12, 70.31, 60; 514/938, 941

(56) References Cited

U.S. PATENT DOCUMENTS

| 4,724,137 A | * | 2/1988 | Hoppe et al. |
| 5,302,376 A | * | 4/1994 | Forestier et al. |
| 5,334,372 A | * | 8/1994 | Kawamata et al. |
| 5,489,431 A | * | 2/1996 | Ascione et al. |
| 5,733,532 A | * | 3/1998 | Raspanti et al. |
| 5,776,494 A | * | 7/1998 | Guskey et al. |
| 5,882,634 A | * | 3/1999 | Allard et al. |
| 6,096,294 A | * | 8/2000 | Hansenne et al. |

FOREIGN PATENT DOCUMENTS

JP  07 033628  3/1995

OTHER PUBLICATIONS

Translation of JP7–33628, referred to as Kao Corp. in the rejection of Oct. 24, 2000.*

* cited by examiner

Primary Examiner—Thurman K. Page
Assistant Examiner—Robert M. Joynes
(74) Attorney, Agent, or Firm—Burns, Doane, Swecker & Mathis, L.L.P.

(57) ABSTRACT

The present application relates to novel oil-in-water emulsions comprising i) at least one specific 1,3,5-triazine derivative and ii) at least one polyalkyl-polyethersiloxane carrying polyoxyalkylene groups grafted onto the main silicone chain; with the proviso that the said emulsions do not comprise cetylstearyltrimethylammonium chloride.

Another subject-matter of the present invention is the use of such emulsions in the manufacture of cosmetic or dermatological compositions intended for the photoprotection of the skin and/or hair and/or other keratinous substances against ultraviolet radiation, in particular solar radiation.

31 Claims, No Drawings

OIL-IN-WATER EMULSIONS CONTAINING A 1,3,5-TRIAZINE DERIVATIVE AND A COPOLYOL SILICONE AND COSMETIC APPLICATIONS

This application is a national stage filing under 35 U.S.C. §371 of International Application No. PCT/FR98/02425 filed on Nov. 13, 1998, which International Application was not published by the International Bureau in English.

The present invention relates to novel oil-in-water emulsions comprising i) at least one specific 1,3,5-triazine derivative and ii) at least one polyalkylpolyethersiloxane carrying polyoxyalkylenated groups grafted onto the main silicone chain, and to their cosmetic uses in the photoprotection of the skin and/or hair and/or other keratinous substances against ultraviolet radiation, in particular solar radiation.

It is known that light radiation with wavelengths of between 280 nm and 400 nm makes it possible to tan the human epidermis and that radiation with wavelengths of between 280 nm and 220 nm, known under the name of UV-B radiation, causes erythemas and cutaneous burns which can be harmful to the development of a natural tan; this UV-B radiation must therefore be screened out.

It is also known that UV-A radiation with wavelengths of between 320 nm and 400 nm, which causes tanning of the skin, can induce a detrimental change in the latter, in particular in the case of sensitive skin or of skin continually exposed to solar radiation. UV-A radiation causes in particular a loss in elasticity of the skin and the appearance of wrinkles, resulting in premature ageing. It promotes the triggering of the erythemal reaction or accentuates this reaction in some subjects and can even be the source of phototoxic or photoallergic reactions. It is therefore desirable also to screen out UV-A radiation.

Numerous cosmetic and/or dermatological compositions intended for the photoprotection (UV-A and/or UV-B) of the skin have been provided to date.

These anti-sun compositions are fairly often provided in the form of an emulsion, of oil-in-water type (that is to say, a cosmetically and/or dermatologically acceptable vehicle composed of a continuous aqueous dispersing phase and of a non-continuous oily dispersed phase) or water-in-oil type (aqueous phase dispersed in a continuous oily phase), which comprises, at various concentrations, one or more conventional lipophilic and/or hydrophilic organic screening agents capable of selectively absorbing harmful UV radiation, these screening agents (and their amounts) being selected according to the desired sun protection factor (the sun protection factor (SPF) being expressed mathematically by the ratio of the irradiation time necessary to reach the erythemal threshold with the UV screening agent to the time necessary to reach the erythemal threshold without the UV screening agent. In such emulsions, the hydrophilic screening agents are present in the aqueous phase and the lipophilic screening agents are present in the fatty phase.

Oil-in-water emulsions are generally more appreciated by the consumer than water-in-oil emulsions, in particular because of their pleasant feel (similar to water) and their presentation in the form of a non-greasy cream or milk, whereas water-in-oil emulsions leave, after application, a feeling of greasiness which is particularly unpleasant to the user.

However, the oil-in-water emulsions commonly used in anti-sun applications require the use of oil-in-water emulsifying surface-active agents, such as polyalkoxylated fatty acids, polyalkoxylated fatty alcohols or certain anionic surfactants, which can exhibit an irritant potential for sensitive skin. The conventional emulsifying surfactants used, as is recalled in the article entitled "Universal Oil-in-water Polyelectrolyte Emulsifiers for Advanced Cosmetic Product Formulation", Parfumerie und Kosmetik, 72, Jahrgang, No. 11/91, emulsify by significantly reducing the oil/water interfacial energies.

To overcome this disadvantage, provision has been made to use, in place of conventional emulsifying surfactants, certain thickening and/or gelling agents, because they make it possible to improve the stability of oil/water emulsions and because they are highly innocuous with regard to sensitive skin. Mention may be made, for example, of crosslinked poly(acrylic acid)s of the Carbopol type, crosslinked poly(acrylic acid)s possessing a fatty chain, such as Pemulen TR1, or modified or unmodified guar gums and celluloses, such as hydroxypropylated guar gum, methylhydroxy-ethylcellulose and hydroxypropylmethyl cellulose. However, the stability of these oil/water emulsions comprising these thickening and/or gelling agents is still not entirely satisfactory.

Certain 1,3,5-triazine derivatives are known in cosmetics for their properties of absorbing UV radiation and more particularly UV-B rays. They are disclosed in Patent Applications EP-A-0,517,104, EP-A-0,570,838 and EP-A-0,796,851. 2,4,6-Tris[p-(2'-ethyl-hexyl-1'-oxycarbonyl)anilino]-1,3,5-triazine, sold in particular under the trade name of "Uvinul T150" by the company BASF, is also known.

Hair compositions for the photoprotection of the hair against the harmful effects of UV rays comprising the combination of a 1,3,5-triazine derivative (i.e.: Uvinul T150) and of a water-insoluble non-volatile silicone, such as a polyalkylpolyethersiloxane (i.e.: KF6002), are also known from Japanese Patent Application JP 07 033 628. Example 7 describes in particular an aqueous conditioning composition comprising the triazine Uvinul T150, a polyalkylpolyethersiloxane (KF6002), cetyl alcohol and cetylstearyltrimethylammonium chloride.

It has been discovered, surprisingly, that, in contrast to other conventional organic UV screening agents commonly used in anti-sun applications, these same 1,3,5-triazine derivatives acted as stabilizing agents in oil-in-water emulsions comprising polyalkylpolyethersiloxanes carrying polyoxyalkylenated groups grafted onto the silicone chain.

The Applicant Company has discovered that the use of these 1,3,5-triazine derivatives, which will be defined in detail later, in combination with polyalkylpolyethersiloxanes carrying polyoxyalkylenated groups grafted onto the silicone chain, in oil-in-water emulsions as defined above comprising at least one water-soluble or hydrophilic gelling and/or thickening agent made it possible to substantially improve the stability of these formulations, without it being necessary to use conventional surface-active emulsifiers.

Furthermore, the Applicant Company has found that the oil-in-water emulsions thus obtained with this specific combination made it possible to prepare cosmetic or dermatological compositions for the photoprotection of the skin and/or hair and/or other keratinous substances which have good absorbing properties with regard to UV rays and which can comprise a broad range of hydrophilic and lipophilic sunscreen agents chosen so as to obtain high sun protection factors and to obtain photoprotection with regard to UV rays within a broad range of wavelengths (UV-A and/or UV-B).

Thus, in accordance with one of the subject-matters of the present invention, novel oil-in-water emulsions are now provided which are essentially characterized in that they comprise i) at least one specific 1,3,5-triazine derivative and ii) at least one polyalkylpolyethersiloxane carrying polyoxyalkylenated groups grafted onto the main silicone chain; with the proviso that the said emulsion does not comprise cetylstearyltrimethylammonium chloride.

Another subject-matter of the present invention is the use of such emulsions in the manufacture of cosmetic or dermatological compositions intended for the protection of the skin and/or hair and/or other human keratinous substances, such as the eyelashes, eyebrows or nails, against ultraviolet radiation, in particular solar radiation.

Yet another subject-matter of the present invention lies in a cosmetic treatment process for the protection of the skin and/or hair and/or other human keratinous substances against ultraviolet radiation, in particular solar radiation, which consists essentially in applying, to the latter, an effective amount of a composition in accordance with the invention.

Another subject-matter of the present invention is the use of the triazine derivatives of the invention as stabilizing agent in the preparation of an oil-in-water emulsion comprising at least one polyalkylpolyethersiloxane carrying polyoxyalkylenated groups grafted onto the silicone chain.

Other characteristics, aspects and advantages of the present invention will become apparent on reading the detailed description which will follow.

The 1,3,5-triazine derivatives in accordance with the invention correspond to the following general formula:

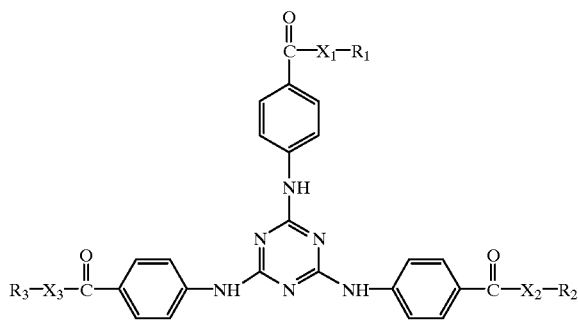

(I)

in which:
$X_1$, $X_2$ and $X_3$, which are identical or different, represent oxygen or an —NR— radical;
the R radicals, which are identical or different, denote hydrogen or a linear or branched $C_1$–$C_{18}$ alkyl radical or a $C_5$–$C_{12}$ cycloalkyl radical which can be substituted by one or more $C_1$–$C_4$ alkyl radicals;
$R_1$, $R_2$ and $R_3$, which are identical or different, are chosen from: hydrogen; an alkali metal; an ammonium radical optionally substituted by one or more alkyl or hydroxyalkyl radicals; a linear or branched $C_1$–$C_{18}$ alkyl radical; a $C_5$–$C_{12}$ cycloalkyl radical optionally substituted by one or more $C_1$–$C_4$ alkyl radicals; a polyoxyethylenated radical comprising from 1 to 6 ethylene oxide units, the terminal OH group of which is methylated; or a radical of the following formula (II), (III) or (IV):

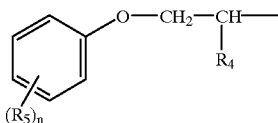

(II)

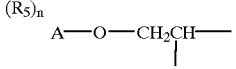

(III)

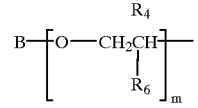

(IV)

in which formulae:
$R_4$ is hydrogen or a methyl radical;
$R_5$ is a $C_1$–$C_9$ alkyl radical;
n is an integer ranging from 0 to 3;
m is an integer ranging from 1 to 10;
A is a $C_4$–$C_8$ alkyl radical or a $C_5$–$C_8$ cycloalkyl radical;

B is chosen from: a linear or branched $C_1$–$C_8$ alkyl radical; a $C_5$–$C_8$ cycloalkyl radical; or an aryl radical optionally substituted by one or more $C_1$–$C_4$ alkyl radicals;
$R_6$ is hydrogen or a methyl radical.

A first preferred family of 1,3,5-triazine derivatives is that, disclosed in particular in the document EP-A-0,517,104 (the teachings of which are, as regards the actual definition of these products, entirely included as reference in the present description), of the 1,3,5-triazines corresponding to the above formula (I) and exhibiting all of the following characteristics:
$X_1$, $X_2$ and $X_3$ are identical and represent oxygen;
$R_1$ is chosen from: a $C_5$–$C_{12}$ cycloalkyl radical optionally substituted by one or more $C_1$–$C_4$ alkyl radicals; or a radical of above formula (II), (III) or (IV), in which formulae:
B is a $C_1$–$C_4$ alkyl radical;
$R_6$ is the methyl radical;
$R_2$ and $R_3$, which are identical or different, are chosen from: hydrogen; an alkali metal; an ammonium radical optionally substituted by one or more alkyl or is hydroxyalkyl radicals; a linear or branched $C_1$–$C_{18}$ alkyl radical; a $C_5$–$C_{12}$ cycloalkyl radical optionally substituted by one or more $C_1$–$C_4$ alkyl radicals; or a radical of above formula (II), (III) or (IV), in which formulae:
B is a $C_1$–$C_4$ alkyl radical;
$R_6$ is the methyl radical.

A second preferred family of 1,3,5-triazine derivatives according to the invention is that, disclosed in particular in the document EP-A-0,570,838 (the teachings of which are, as regards the actual definition of these products, entirely included as reference in the present description), of the 1,3,5-triazines corresponding to the formula (I) and exhibiting all of the following characteristics:
$X_1$ is oxygen; $X_2$ is the NH radical or oxygen;
$X_3$ is the —NH— radical;
$R_3$ is chosen from: a linear or branched $C_1$–$C_{18}$ alkyl radical; or a $C_5$–$C_{12}$ cycloalkyl radical optionally substituted with one or more $C_1$–$C_4$ alkyl radicals;
$R_1$ is chosen from: hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals;
if $X_2$ is the —NH— radical, then $R_2$ is chosen from: a linear or branched $C_1$–$C_{18}$ alkyl radical; or a $C_5$–$C_{12}$ cycloalkyl radical optionally substituted with one or more $C_1$–$C_4$ alkyl radicals;
if $X_2$ is oxygen, then $R_2$ is chosen from hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals.

A third preferred family of 1,3,5-triazine derivatives according to the invention is that, disclosed in particular in the document EP-A-0,796,851 (the teachings of which are, as regards the actual definition of these products, entirely included by way of reference in the present description), of the 1,3,5-triazines corresponding to the formula (I) and exhibiting all of the following characteristics:
$X_1$, $X_2$ and $X_3$ simultaneously denote —NR—;
the R radicals, which are identical or different, denote hydrogen or a linear or branched $C_1$–$C_{18}$ alkyl radical or a $C_5$–$C_{12}$ cycloalkyl radical which can be substituted by one or more $C_1$–$C_4$ alkyl radicals;
$R_1$, $R_2$ and $R_3$, which are identical or different, denote hydrogen or an R radical.

A particularly preferred 1,3,5-triazine according to the invention is that corresponding to the following formula:

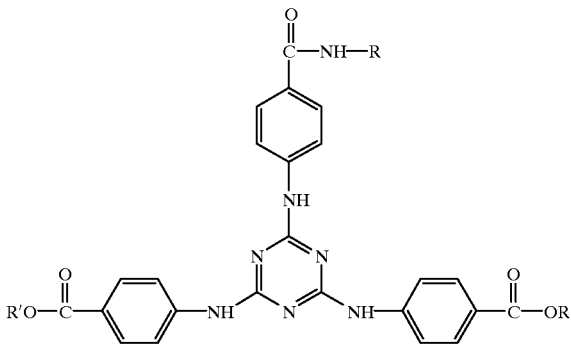

in which R' denotes a 2-ethylhexyl radical and R denotes a tert-butyl radical.

Another particularly preferred 1,3,5-triazine is 2,4,6-tris [p-(2'-ethylhexyl-1'-oxycarbonyl)anilino]-1,3,5-triazine, which is a screening agent known per se active in the UV-B, which is provided in a solid form and which is sold in particular under the trade name of "Uvinul T150" by the company BASF. This product corresponds to the following formula:

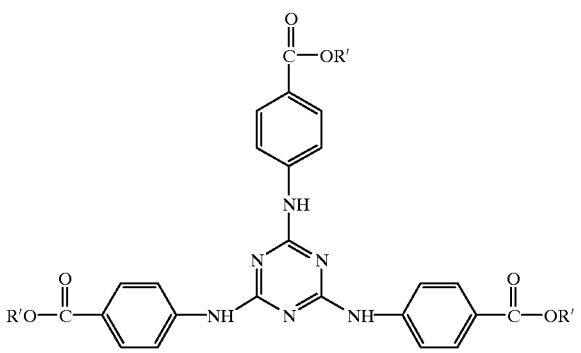

in which R' denotes a 2-ethylhexyl radical.

The 1,3,5-triazine derivative or derivatives are generally present in the compositions of the invention at a content which can range from 0.5% to 20%, preferably from 1% to 10%, by weight with respect to the total weight of the composition.

The compositions in accordance with the invention comprise a polyalkylpolyethersiloxane carrying polyalkoxylated chains on the main chain and more preferably polyoxyethylene and/or polyoxypropylene chains grafted onto the main chain.

More particularly, the polyalkylpolyethersiloxanes of the invention are chosen from the compounds of following general formula (V):

(V)

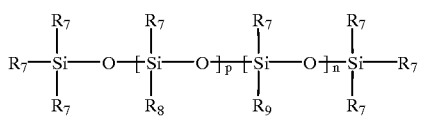

in which formula:
$R_7$ and $R_9$, which are identical or different, represent a hydrogen atom, a linear or branched $C_1$–$C_{30}$ alkyl radical or a phenyl radical, $R_8$, which are identical or different, represent $(C_xH_{2x})$—$(OC_2H_4)_a$—$(OC_3H_6)_b$—$OR_{10}$, $R_{10}$, which are identical or different, are chosen from a hydrogen atom, a linear or branched alkyl radical having from 1 to 12 carbon atoms or a linear or branched acyl radical having from 2 to 12 carbon atoms, n varies from 1 to 1000, p varies from 1 to 30, a varies from 1 to 50, b varies from 0 to 50, x varies from 1 to 5.

The number-average molecular weight of silicone compound is generally greater than or equal to 15,000 and preferably between 20,000 and 40,000.

A first family of polyalkylpolyethersiloxanes particularly well suited to the compositions according to the invention is that of the compounds corresponding to the above formula (V) in which the $R_7$ and $R_9$ radicals are identical and all represent methyl radicals and the $R_{10}$ radical represents hydrogen.

Mention may be made, as an example of a silicone compound belonging to this family, of the oxyethylenated polydimethylsiloxane (9/4) (12 EO) supplied by the company Dow Corning under the name "DC 193"; or the oxyethylenated and oxypropylenated polydimethyl/methylsiloxane (EO/PO 18/18), in which n is 396 and p is 4, with a number-average molecular weight of greater than 30,000 (CTFA name: Cyclomethicone 90% Dimethicone copolyol 10%), sold under the trade name of "Silicone DC 3225C" by the company Dow Corning.

In the above definition and in the continuation of the text, EO represents one mole of ethylene oxide and PO represents one mole of propylene oxide.

A second family of polyalkylpolyethersiloxanes particularly well suited to the compositions according to the invention is that of the compounds corresponding to the above formula (V) in which the $R_7$ radicals all represent methyl radicals and the $R_9$ radicals all represent lauryl radicals.

A particularly preferred compound of this second family is the oxyethylenated-oxypropylenated polymethyllauryl/methylsiloxane (EO/OP 18/18), in which n is 35 and p is 3, with a number-average molecular weight greater than 25,000 (CTFA name: Laurylmethicone copolyol 91%, Isostearyl alcohol 9%), sold under the trade name "DC Q2-5200" by the company Dow Corning.

The polyalkylpolyethersiloxane or polyalkylpolyethersiloxanes of the inventions are generally present in the compositions according to the invention in a proportion of active material of between 0.2% and 5% by weight, preferably between 0.25% and 3% by weight, with respect to the total weight of the composition.

The oil-in-water emulsions in accordance with the invention generally comprise at least one water-soluble or hydrophilic thickening and/or gelling agent. They preferably comprise less than 0.5% by weight of conventional emulsifying surface-active agent with respect to the total weight of the composition and more particularly are devoid of conventional emulsifying surface-active agent.

Mention may be made, as thickening and/or gelling agent which can be used, of:
algal extracts, such as agar-agar, carrageenans and alginates;
seed extracts, such as locust bean gum, guar gum and their derivatives;
plant exudates, such as gum arabic, karaya gum, gum tragacanth or ghatti gum;
microorganism exudates, such as xanthan gum, cellulose or its derivatives, such as carboxymethylcellulose, hydroxypropylcellulose, methylcellulose, hydroxypropylmethylcellulose or hydroxyethylcellulose, as well as modified celluloses, in particular modified by grafting an alkyl group;

fruit extracts, such as pectins;

gelling agents of animal origin, such as caseinates;

synthetic polymers;

silicon derivatives, such as synthetic hectorites, for example the products "Laponite RD and RDS" sold by the company Waverly, or aluminium magnesium silicates, such as the product "Veegum" sold by the company Vanderbilt, the mixtures of the above compounds.

The preferred synthetic thickening and/or gelling polymers are chosen from:

(a) acrylic acid homopolymers crosslinked by an allyl ether of an alcohol of the sugar series, such as the products sold under the names Carbopols 980, 981, 954, 2984 and 5984 by the company Goodrich or the products sold under the names Synthalen M and Synthalen K by the company 3 VSA;

(b) crosslinked copolymers comprising a major fraction of acrylic acid and a small fraction of $C_{10}$–$C_{30}$ esters of (meth)acrylic acid, such as the products sold under the names Pemulen TR1, Pemulen TR2 and Carbopol 1342 by the company Goodrich (they are disclosed and prepared in the document EP-A-268,164);

(c) crosslinked homopolymers of 2-acrylamido-2-methylpropanesulphonic acid, such as those disclosed in Application EP-A-0,815,828, and their partially or completely neutralized (by a base, such as sodium hydroxide, potassium hydroxide or an amine) crosslinked copolymers with acrylamide, such as the product disclosed in Example 1 of the document EP-A-503,853;

(d) ammonium acrylate homopolymers, such as the product sold under the name Microsap PAS 5193 by the company Hoechst, or copolymers of ammonium acrylate and of acrylamide, such as the product sold under the name Bozepol C Nouveau [New] or the product PAS 5193, which are sold by the company Hoechst (they are disclosed and prepared in the documents FR 2,416,723, U.S. Pat. No. 2,798,053 and U.S. Pat. No. 2,923,692);

(e) homopolymers of dimethylaminoethyl methacrylate which is quaternized by methyl chloride, such as the products sold under the names Salcare 95 and Salcare 96 by the company Allied Colloids, or copolymers of dimethylaminoethyl methacrylate, which is quaternized by methyl chloride, and of acrylamide, such as the product Salcare $SC_{92}$ sold by Allied Colloids or the product PAS 5194 sold by Hoechst (they are disclosed and prepared in the document EP-A-395,282).

The thickening and/or gelling agents are used in concentrations preferably ranging from 0.1 to 10% by weight, in particular from 0.1 to 5% by weight, with respect to the total weight of the composition.

The compositions according to the invention also comprise an oily phase which can comprise one or more fatty substances, it being possible for these fatty substances to be composed of an oil or a wax or their mixtures. The term "oil" is understood to mean a compound which is liquid at room temperature. The term "wax" is understood to mean a compound which is solid or substantially solid at room temperature and which has a melting point generally of greater than 35° C.

Mention may be made, as oils, of mineral oils (petrolatum), vegetable oils (sweet almond oil, macadamia oil, blackcurrant seed oil or jojoba oil), synthetic oils, such as perhydrosqualene, fatty alcohols, acids or esters (such as the benzoate of $C_{12}$–$C_{15}$ alcohols sold under the trade name "Finsolv TN" by the company Finetex, octyl palmitate, isopropyl lanolate or triglycerides, including those of capric/caprylic acids) or oxyethylenated or oxypropylenated fatty esters and ethers, fluorinated oils or else polyalkylenes, such as polydecene.

Mention may be made, as waxy compounds, of paraffin wax, carnauba wax, beeswax or hydrogenated castor oil.

The oily phase can also comprise a volatile or non-volatile silicone oil, such as cyclomethicones or dimethicones. Use may be made in the compositions of the present invention of, for example, a volatile silicone oil, such as, for example, the cyclomethicones sold under the trade names "$DC_{245}$ Fluid" or "DC246 Fluid" by Dow Corning.

The cosmetic and/or dermatological compositions targeted by the present invention can, of course, comprise one or more hydrophilic or lipophilic sunscreen agents which are active in the UV-A and/or UV-B (absorbers). These screening agents can in particular be chosen from cinnamic derivatives, salicylic derivatives, dibenzoylmethane derivatives, benzylidenecamphor derivatives, benzimidazole derivatives, benzophenone derivatives, β, β'-diphenylacrylate derivatives, p-aminobenzoic acid derivatives, or the screening polymers and screening silicones disclosed in Application WO-93/04665. Other examples of organic screening agents are given in Patent Application EP-AO,487,404.

Mention may be made, as hydrophilic screening agents which can particularly be used in the present invention, of benzene-1,4-di(3-methylidene-10-camphorsulphonic acid) and 2-phenylbenzimidazole-5-sulphonic acid, sold under the trade name "Eusolex 232" by the company Merck, or their mixture.

Mention may be made, as lipophilic screening agents which can particularly be used in the present invention, of 4-tert-butyl-4'-methoxydibenzoylmethane, sold under the trade name "Parsol 1789" by the company Givaudan, and/or 2-ethylhexyl α-cyano-β, β-diphenylacrylate, sold under the trade name "Uvinul N 539" by the company BASF.

The hydrophilic screening agent or agents can be present in the final composition according to the invention at a content which can vary from 0.1 to 20%, preferably from 0.2 to 10%, by weight with respect to the total weight of the composition. The lipophilic screening agent or agents can be present in the final composition according to the invention at a content which can vary from 0.5 to 30%, preferably from 0.5 to 20%, by weight with respect to the total weight of the composition.

The cosmetic and/or dermatological compositions according to the invention can also comprise coated or non-coated metal oxide pigments or alternatively nanopigments (mean size of the primary particles: generally between 5 nm and 100 nm, preferably between 10 and 50 nm), such as, for example, titanium oxide (amorphous or crystallized in rutile and/or anatase form), iron oxide, zinc oxide, zirconium oxide or cerium oxide nanopigments, which are all photoprotective agents well known per se which act by physically blocking (reflecting and/or scattering) UV radiation. Conventional coating agents are, furthermore, alumina and/or aluminium stearate or silicones. Such coated or non-coated metal oxide nanopigments are disclosed in particular in Patent Application EP-A-0,518,772 and EP-A-0,518,773.

The nanopigments can be present in the final composition according to the invention at a content which can vary from 0.1 to 20%, preferably from 0.2 to 10%, by weight with respect to the total weight of the composition.

The compositions according to the invention can also comprise agents for the artificial tanning and/or browning of the skin (self-tanning agents), such as, for example, dihydroxyacetone (DHA).

The compositions in accordance with the present invention can furthermore comprise conventional cosmetic and/or dermatological adjuvants chosen in particular from organic solvents, softeners, antioxidants, agents for combating free radicals, opacifiers, stabilizers, emollients, α-hydroxy acids, antifoaming agents, moisturizing agents, vitamins, fragrances, preservatives, surfactants, fillers, sequestering agents, polymers, propellants, basifying or acidifying agents, dyes or any other ingredient commonly used in the cosmetics and/or dermatological field, in particular for the manufacture of anti-sun compositions in the form of emulsions.

Of course, a person skilled in the art will take care to choose the optional additional compound or compounds mentioned above and/or their amounts so that the advantageous properties intrinsically attached to the binary combination in accordance with the invention are not, or not substantially, detrimentally affected by the envisaged addition or additions.

The compositions according to the invention can be prepared according to the techniques for the preparation of emulsions of oil-in-water type which are well known to a person skilled in the art.

The cosmetic and/or dermatological composition of the invention can be used as a composition for protecting the human epidermis and/or hair and/or other human keratinous substances, such as the eyelashes, eyebrows or nail, against ultraviolet rays, as an anti-sun composition or as a make-up product.

Concrete but in no way limiting examples illustrating the invention will now be given.

EXAMPLE 1
Oil-in-water Emulsion

| | |
|---|---|
| 2,4,6-Tris[p-(2'-ethylhexyl-1'-oxycarbonyl)anilino]-1,3,5-triazine, sold under the name "Uvinul T 150" by the company BASF | 2.5% by weight |
| Oxyethylenated polydimethylsiloxane (9/4) (12 EO), supplied by the company Dow Corning under the name "DC 193" | 1.5% by weight |
| Crosslinked 2-acrylamido-2-methylpropanesulphonic acid/acrylamide copolymer, sold under the name "Sepigel 305" by the company SEPPIC | 4.0% by weight |
| Benzoate of $C_{12}/C_{15}$ alcohols, sold under the trade name "Finsolv TN" by Finetex | 25% by weight |
| Moisturizers | 12% by weight |
| Denatured alcohol | 4.5% by weight |
| Preservatives | q.s. |
| Purified water | q.s. for 100% by weight |

The formulation does not separate into distinct phases after centrifuging at 2000 revolutions/minute for 30 minutes and remains stable after storage for two months at 450° C.

EXAMPLE 2
(not forming part of the invention): Oil-in-water Emulsion

| | |
|---|---|
| Oxyethylenated polydimethylsiloxane (9/4) (12 EO), supplied by the company Dow Corning under the name "DC 193" | 1.5% by weight |
| Crosslinked 2-acrylamido-2-methylpropanesulphonic acid/acrylamide copolymer, sold under the name "Sepigel 305" by the company SEPPIC | 4.0% by weight |
| Benzoate of $C_{12}/C_{15}$ alcohols, sold under the trade name "Finsolv TN" by Finetex | 27.5% by weight |
| Moisturizers | 12% by weight |
| Denatured alcohol | 4.5% by weight |
| Preservatives | q.s. |
| Purified water | q.s. for 100% by weight |

The formulation separates out after centrifuging at 3000 revolutions/minute for 30 minutes and after storage for two months at 450° C., phase separation is observed.

EXAMPLE 3
Anti-sun Composition

| | |
|---|---|
| 2,4,6-Tris[p-(2'-ethylhexyl-1'-oxycarbonyl)anilino]-1,3,5-triazine, sold under the name "Uvinul T 150" by the company BASF | 2.0% by weight |
| 2-Ethylhexyl α-cyano-β,β-diphenylacrylate, sold under the trade name "Uvinul N 539" by BASF | 10% by weight |
| Octyl methoxycinnamate, sold under the trade name "Parsol MCX" by the company Givaudan | 5.0% by weight |
| Benzene-1,4-di(3-methylidene-10-camphorsulphonic acid) | 0.5% by weight |
| Isononyl isononanoate | 2.0% by weight |
| Benzotriazole screening silicone of following formula | 3% by weight |

| | |
|---|---|
| α,ω-Dihydroxyl polydimethylsiloxane/polydimethylsiloxane mixture, sold under the name "Dow Corning DC 1403 Fluid" by the company Dow Corning | 4.0% by weight |
| Oxyethylenated polydimethylsiloxane (9/4) (12 EO), supplied by the company Dow Corning under the name "DC 193" | 1.5% by weight |
| Cocoglycerides, sold under the name "Myritol 331" by the company Henkel | 3.0% by weight |
| Crosslinked 2-acrylamido-2-methylpropanesulphonic acid/acrylamide copolymer, sold under the name "Sepigel 305" by the company SEPPIC | 4.0% by weight |
| Moisturizers | 12% by weight |
| Preservatives q.s. | |
| Triethanolamine q.s. pH 7 | |
| Purified water q.s. for | 100% by weight |

The formulation does not separate out after centrifuging at 3000 revolutions/minute for 30 minutes and remains stable after storage for two months at 45° C.

EXAMPLE 4

(not forming part of the invention): Anti-sun Composition

| | |
|---|---|
| 2-Ethylhexyl α-cyano-β,β-diphenylacrylate, sold under the trade name "Uvinul N 539" by BASF | 10% by weight |
| Octyl methoxycinnamate, sold under the trade name "Parsol MCX" by the company Givaudan | 7.0% by weight |
| Benzene-1,4-di(3-methylidene-10-camphorsulphonic acid) | 0.5% by weight |
| Isononyl isononanoate | 2.0% by weight |
| Benzotriazole screening silicone of following formula | 3% by weight |

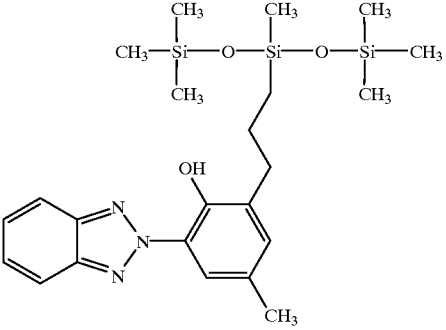

| | |
|---|---|
| α,ω-Dihydroxyl polydimethylsiloxane/polydimethylsiloxane mixture, sold under the name "Dow Corning DC 1403 Fluid" by the company Dow Corning | 4.0% by weight |
| Oxyethylenated polydimethylsiloxane (9/4) (12 EO), supplied by the company Dow Corning under the name "DC 193" | 1.5% by weight |
| Cocoglycerides, sold under the name "Myritol 331" by the company Henkel | 3.0% by weight |
| Crosslinked 2-acrylamido-2-methylpropanesulphonic acid/acrylamide copolymer, sold under the name "Sepigel 305" by the company SEPPIC | 4.0% by weight |
| Moisturizers | 12% by weight |
| Preservatives q.s. | |
| Triethanolamine q.s. pH 7 | |
| Purified water q.s. for | 100% by weight |

The formulation separates out after storage for two months at 45° C. The replacement in Example 4 of the triazine derivative (2% by weight) by octyl methoxycinnamate does not make it possible to stabilize the oil-in-water emulsion comprising the silicone copolyol.

EXAMPLE 5

Anti-sun Composition

| | |
|---|---|
| 2,4,6-Tris[p-(2'-ethylhexyl-1'-oxycarbonyl)anilino]-1,3,5-triazine, sold under the name "Uvinul T 150" by the company BASF | 1.0% by weight |
| 2-Ethylhexyl α-cyano-β,β-diphenylacrylate, sold under the trade name "Uvinul N 539" by BASF | 2.1 by weight |
| 4-tert-Butyl-4'-methoxydibenzoylmethane, sold under the trade name "Parsol 1789" by Givaudan | 0.9% by weight |
| Benzene-1,4-di (3-methylidene-10-camphorsulphonic acid) | 0.5% by weight |
| Stearyl heptanoate | 2.0% by weight |
| Titanium dioxide (UV Titan M160 from Kenmira) | 0.5% by weight |
| Acrylic acid/$C_{10}$–$C_{30}$ alkyl acrylate copolymer, sold under the trade name "Pemulen TR-1" by the company Goodrich | 0.4% by weight |
| K hexadecyl phosphate, sold under the trade name "Amphisol K" by Roche | 0.2% by weight |
| Oxyethylenated-oxypropylenated polydimethyl/methylsiloxane (396/4) (EO/PO 18/18), supplied under the name "DC 3225 C" by the company Dow Corning | 1.0% by weight |
| Volatile silicone | 5.0% by weight |
| Stearate oligomer of 12-hydroxystearic acid, sold under the name Solsperse 21000 | 0.05% by weight |
| Benzoate of $C_{12}$/$C_{15}$ alcohols, sold under the trade name "Finsolv TN" by Finetex | 6.0% by weight |
| Moisturizers | 12% by weight |
| Preservatives | q.s. |
| Triethanolamine | q.s. pH 7 |
| Purified water | q.s. for 100% by weight |

The formulation does not separate out after centrifuging at 3000 revolutions/minute for 30 minutes and remains stable after storage for two months at 45° C.

EXAMPLE 6

(not forming part of the invention): Anti-sun Composition

| | |
|---|---|
| 2-Ethylhexyl α-cyano-β,β-diphenylacrylate, sold under the trade name "Uvinul N 539" by BASF | 2.1% by weight |
| 4-tert-Butyl-4'-methoxy-dibenzoylmethane, sold under the trade name "Parsol 1789" by Givaudan | 0.9% by weight |
| Benzene-1,4-di (3-methylidene-10-camphorsulphonic acid) | 0.5% by weight |
| Stearyl heptanoate | 2.0% by weight |
| Titanium dioxide (UV Titan M160 from Kenmira) | 0.5% by weight |
| Acrylic acid/$C_{10}$–$C_{30}$ alkyl acrylate copolymer, sold under the trade name "Pemulen TR-1" by the company Goodrich | 0.4% by weight |
| K hexadecyl phosphate, sold under the trade name "Amphisol K" by Roche | 0.2% by weight |
| Oxyethylenated-oxypropylenated polydimethyl/methylsiloxane (396/4) (EO/PO 18/18), supplied under the name "DC 3225 C" by the company Dow Corning | 1.0% by weight |
| Volatile silicone | 5.0% by weight |
| Stearate oligomer of 12-hydroxystearic acid, sold under the name Solsperse 21000 | 0.05% by weight |
| Benzoate of $C_{12}$/$C_{15}$ alcohols, sold under the trade name "Finsolv TN" by Finetex | 7.0% by weight |
| Moisturizers | 12% by weight |
| Preservatives | q.s. |

| | |
|---|---|
| Triethanolamine | q.s. pH 7 |
| Purified water | q.s. for 100% by weight |

The formulation separates out after centrifuging at 3000 revolutions/minute for 30 minutes.

What is claimed is:

1. Oil-in-water emulsion, comprising at least:
   i) one 1,3,5-triazine derivative of the following formula:

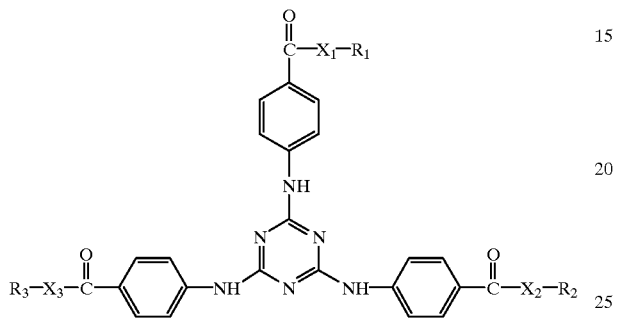

(I)

in which:

$X_1$, $X_2$ and $X_3$, which are identical or different, represent oxygen or an —NR— radical;

the R radicals, which are identical or different, denote hydrogen or a linear or branched $C_1$–$C_{18}$ alkyl radical or a $C_5$–$C_{12}$ cycloalkyl radical which can be substituted by one or more $C_1$–$C_4$ alkyl radicals;

$R_1$, $R_2$ and $R_3$, which are identical or different, comprises hydrogen; an alkali metal; an ammonium radical optionally substituted by one or more alkyl or hydroxyalkyl radicals; a linear or branched $C_1$–$C_{18}$ alkyl radical; a $C_5$–$C_{12}$ cycloalkyl radical optionally substituted by one or more $C_1$–$C_4$ alkyl radicals; a polyoxyethylenated radical comprising from 1 to 6 ethylene oxide units, the terminal OH group of which is methylated; or a radical of the following formula (II), (III) or (IV):

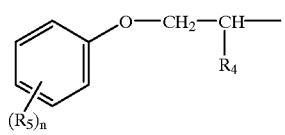

(II)

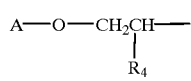

(III)

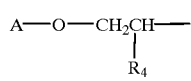

(IV)

in which formulae:

$R_4$ is hydrogen or a methyl radical;
$R_5$ is a $C_1$–$C_9$ alkyl radical;
n is an integer ranging from 0 to 3;
m is an integer ranging from 1 to 10;
A is a $C_4$–$C_8$ alkyl radical or a $C_5$–$C_8$ cycloalkyl radical;

B comprises a linear or branched $C_1$–$C_8$ alkyl radical; a $C_5$–$C_8$ cycloalkyl radical; or an aryl radical optionally substituted by one or more $C_1$–$C_4$ alkyl radicals;

$R_6$ is hydrogen or a methyl radical; and ii) one polyalkylpolyethersiloxane carrying polyoxyalkylenated groups grafted onto the main silicone chain; with the proviso that said emulsion does not comprise cetylstearyltrimethylammonium chloride.

2. Emulsion according to claim 1, where the 1,3,5-triazine derivatives of formula (I) exhibit all of the following characteristics:

$X_1$, $X_2$ and $X_3$ are identical and represent oxygen;

$R_1$ comprises: a $C_5$–$C_{12}$ cycloalkyl radical optionally substituted by one or more $C_1$–$C_4$ alkyl radicals; or a radical of above formula (II), (III) or (IV), in which formulae:

B is a $C_1$–$C_4$ alkyl radical;

$R_6$ is the methyl radical;

$R_2$ and $R_3$, which are identical or different, comprises: hydrogen; an alkali metal; an ammonium radical optionally substituted by one or more alkyl or hydroxyalkyl radicals; a linear or branched $C_1$–$C_{18}$ alkyl radical; a $C_5$–$C_{12}$ cycloalkyl radical optionally substituted by one or more $C_1$–$C_4$ alkyl radicals; or a radical of above formula (II), (III) or (IV), in which formulae:

B is a $C_1$–$C_4$ alkyl radical;

$R_6$ is the methyl radical.

3. Emulsion according to claim 1, where the 1,3,5-triazine derivatives of formula (I) exhibit all of the following characteristics:

$X_1$ is oxygen; $X_2$ is the NH radical or oxygen;

$X_3$ is the —NH— radical;

$R_3$ comprises a linear or branched $C_1$–$C_{18}$ alkyl radical; or a $C_5$–$C_{12}$ cycloalkyl radical optionally substituted with one or more $C_1$–$C_4$ alkyl radicals;

$R_1$ comprises: hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals;

if $X_2$ is the —NH— radical, then $R_2$ is chosen from: a linear or branched $C_1$–$C_{18}$ alkyl radical; or a $C_5$–$C_{12}$ cycloalkyl radical optionally substituted with one or more $C_1$–$C_4$ alkyl radicals;

if $X_2$ is oxygen, then $R_2$ is chosen from hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals.

4. Emulsion according to claim 1, where the 1,3,5-triazine derivatives of formula (I) exhibit all of the following characteristics:

$X_1$, $X_2$ and $X_3$ simultaneously denote —NR—;

the R radicals, which are identical or different, denote hydrogen or a linear or branched $C_1$–$C_{18}$ alkyl radical or a $C_5$–$C_{12}$ cycloalkyl radical which can be substituted by one or more $C_1$–$C_4$ alkyl radicals;

$R_1$, $R_2$ and $R_3$, which are identical or different, denote hydrogen or an R radical.

5. Emulsion according to claim 1, where the 1,3,5-triazine derivative corresponds to the following formula:

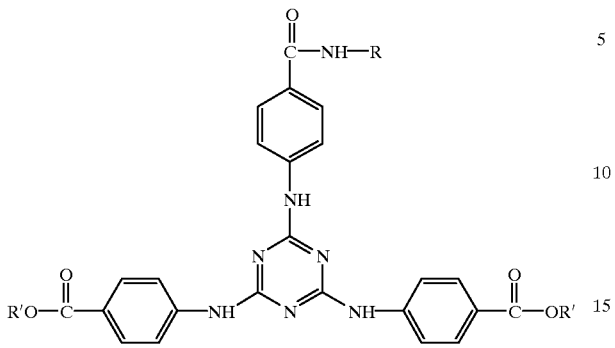

in which R' denotes a 2-ethylhexyl radical and R denotes a tert-butyl radical.

6. Emulsion according to claim 1, where the 1,3,5-triazine derivative corresponds to the following formula:

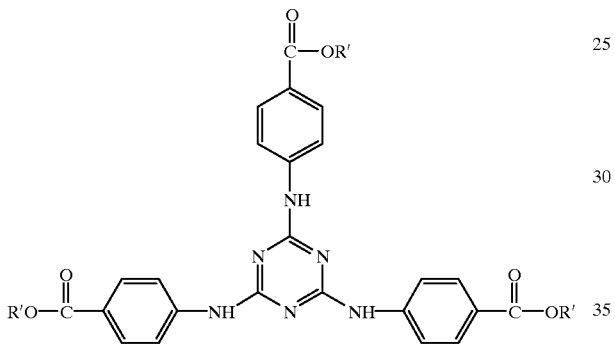

in which R' denotes a 2-ethylhexyl radical.

7. Emulsion according to claim 1, where the 1,3,5-triazine derivatives are present at a content ranging from 0.5% to 20%, by weight with respect to the total weight of the composition.

8. Emulsion according to claim 1, where the polyalkylpolyethersiloxanes comprise polyoxyethylene and/or polyoxypropylene chains grafted onto the main chain.

9. Emulsion according to claim 1, where the polyalkylpolyethersiloxanes comprise the compounds of the following formula (V):

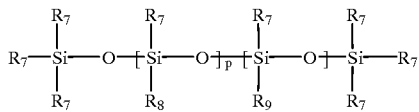

(V)

in which formula:

$R_7$ and $R_9$, which are identical or different, represent a hydrogen atom, a linear or branched $C_1$–$C_{30}$ alkyl radical or a phenyl radical, $R_8$, which are identical or different, represent $(C_xH_{2x})$—$(OC_2H_4)_a$—$(OC_3H_6)_b$—$OR_{10}$, $R_{10}$, which are identical or different, comprise a hydrogen atom, a linear or branched alkyl radical having from 1 to 12 carbon atoms or a linear or branched acyl radical having from 2 to 12 carbon atoms, n varies from 1 to 1000,
p varies from 1 to 30,
a varies from 1 to 50,
b varies from 0 to 50,
x varies from 1 to 5.

10. Emulsion according to claim 1, where the polyalkylpolyethersiloxanes exhibit a number-average molecular weight of greater than or equal to 15,000.

11. Emulsion according to claim 9, where the polyalkylpolyethersiloxanes correspond to the formula (V) in which the $R_7$ and $R_9$ radicals are identical and all represent methyl radicals and the $R_{10}$ radical represents hydrogen.

12. Emulsion according to claim 9, where the polyalkylpolyethersiloxanes correspond to the formula (V) in which the $R_7$ radicals all represent methyl radicals and the $R_9$ radicals all represent lauryl radicals.

13. Emulsion according to claim 1, where the polyalkylpolyethersiloxanes are present in a proportion of active material ranging from 0.2% to 5% by weight, preferably from 0.25% to 3% by weight, with respect to the total weight of the composition.

14. Emulsion according to claim 1, additionally comprising at least one water-soluble or hydrophilic thickening and/or gelling agent.

15. Emulsion according to claim 1, comprising less than 0.5% by weight of emulsifying surface-active agent.

16. Emulsion according to claim 1, wherein it does not comprise a emulsifying surface-active agent.

17. Emulsion according to claim 14, where the thickening and/or gelling agent comprises:

algal extracts;
seed extracts;
plant exudates;
microorganism exudates;
cellulose or its derivatives, as well as modified celluloses;
food extracts;
gelling agents of animal origin;
synthetic polymers;
silicon derivatives,
mixtures of the above compounds.

18. Emulsion according to claim 17, where the synthetic thickening and/or gelling polymers comprise:

(a) acrylic acid homopolymers crosslinked by an allyl ether of an alcohol of the sugar series;
(b) crosslinked copolymers comprising a major fraction of acrylic acid and a minor fraction of $C_{10}$–$C_{30}$ esters of (meth)acrylic acid;
(c) crosslinked homopolymers of 2-acrylamido-2-methylpropanesulphonic acid and their partially or completely neutralized crosslinked copolymers with acrylamide;
(d) ammonium acrylate homopolymers or copolymers of ammonium acrylate and of acrylamide;
(e) homopolymers of dimethylaminoethyl methacrylate quaternized by methyl chloride or copolymers of dimethylaminoethyl methacrylate quaternized by methyl chloride and of acrylamide.

19. Emulsion according to claim 14, where the thickening and/or gelling agents are used in concentrations ranging from 0.1 to 10% by weight, with respect to the total weight of the composition.

20. A method for the protection of the skin and/or hair and other human keratinous substances against ultraviolet radiation comprising administering an effective amount of the oil-in-water emulsion according to claim 1.

21. Cosmetic and/or dermatological composition, comprising at least one oil-in-water emulsion according to claim 7.

22. Composition according to claim 21, additionally comprising one or more one or more hydrophilic or lipophilic sunscreen agents active in the UV-A or UV-B.

23. Composition according to claim 22, where the additional screening agents comprise cinnamic derivatives, salicylic derivatives, dibenzoylmethane derivatives, benzylidenecamphor derivatives, benzimidazole derivatives, benzophenone derivatives, β,β'-diphenylacrylate derivatives, p-aminobenzoic acid derivatives, or screening polymers and screening silicones.

24. Composition according to claim 22 or where the additional hydrophilic screening agent is benzene-1,4-di(3-methylidene-10-camphosulphonic acid) and/or 2-phenylbenzimidazole-5-sulphonic acid.

25. Composition according to claim 22 where the additional lipophilic screening agent is 4-tert-butyl-4'-methoxydibenzoylmethane and/or 2-ethylhexyl α-cyano-β,β-diphenylacrylate.

26. Composition according to claim 21, additionally comprising at least one coated or non-coated metal oxide pigment or nanopigment.

27. Composition according to claim 21, additionally comprising at least one agent for the tanning and/or artificial browning of the skin.

28. Cosmetic treatment process for the protection of the skin and/or the hair and/or the other human keratinous substances against ultraviolet radiation, comprising applying, to the latter, an effective amount of an oil-in-water emulsion as defined according to claim 1 or of a composition as defined according to any one of claims 21 to 27.

29. A method for stabilizing a preparation of an oil-in-water emulsion comprising at least one polyalkylpolyethersiloxane carrying polyoxyalkylene groups grafted onto the silicone chain comprising adding a 1,3,5-triazine derivative according to claim 1.

30. The oil-in-water emulsion of claim 6, comprising 2.5 % by weight of 2,4,6-tris[p-(2'-ethylhexyl-1'-oxycarbonyl) anilino]-1,3,5-triazine and 1.5% by weight of the polyalkylpolyethersiloxane, which is oxyethylenated polydimethylsiloxane.

31. The oil-in-water emulsion of claim 6, comprising 1.0% by weight of 2,4,6-tris[p-(2'-ethylhexyl-1'-oxycarbonyl)anilino]-1,3,5-triazine and 1.0% by weight of the polyalkylpolyethersiloxane, which is oxyethylenated-oxypropylenated polydimethyllmethylsiloxane.

* * * * *